(12) United States Patent
Yamamoto et al.

(10) Patent No.: US 6,767,020 B2
(45) Date of Patent: Jul. 27, 2004

(54) SUSPENSION BUSHING, MOTOR VEHICLE AND A SUSPENSION CROSS-MEMBER FOR A MOTOR VEHICLE

(75) Inventors: Tadanobu Yamamoto, Aki-gun (JP); Susumu Sano, Aki-gun (JP); Tadashi Yoshimura, Aki-gun (JP)

(73) Assignee: Mazda Motor Corporation, Hiroshima (JP)

( * ) Notice: Subject to any disclaimer, the term of this patent is extended or adjusted under 35 U.S.C. 154(b) by 108 days.

(21) Appl. No.: 10/252,108

(22) Filed: Sep. 23, 2002

(65) Prior Publication Data

US 2003/0079311 A1 May 1, 2003

(30) Foreign Application Priority Data

Sep. 28, 2001 (JP) .................................. 2001-299300

(51) Int. Cl.[7] .............................................. B62D 21/11
(52) U.S. Cl. .......................... 280/124.109; 280/124.162
(58) Field of Search .................. 280/124.109, 124.162, 280/124.164, 124.165, 124.169, 124.177; 267/141.2, 141.3, 141.4

(56) References Cited

U.S. PATENT DOCUMENTS

| 4,109,979 | A | | 8/1978 | Estaque |
| 4,531,761 | A | * | 7/1985 | von Sivers .................. 280/785 |
| 5,131,619 | A | * | 7/1992 | Daugherty et al. ......... 248/635 |
| 5,328,160 | A | * | 7/1994 | McLaughlin ............. 267/141.3 |
| 5,961,219 | A | * | 10/1999 | Maughan .................... 384/220 |
| 6,641,151 | B1 | * | 11/2003 | Zetterstrom .......... 280/124.107 |
| 6,666,438 | B2 | * | 12/2003 | Nakagawa ............... 267/141.2 |

FOREIGN PATENT DOCUMENTS

| JP | 2000-145854 | 5/2000 |
| JP | 2001-071944 | 3/2001 |

* cited by examiner

Primary Examiner—Paul N. Dickson
Assistant Examiner—Faye M. Fleming
(74) Attorney, Agent, or Firm—Nixon Peabody LLP; Donald R. Studebaker

(57) ABSTRACT

A pair of bushing including an outer member having an outer main body and an outer flange; an inner member having an inner main body inserted into the outer member, an inner flange, and a through hole; and an elastic member disposed between the outer member and the inner member. The bushings are press-fit into a top aperture and a bottom aperture of a bushing-attaching hole in a suspension cross-member, respectively. When each bushing is press-fit into the apertures there exists a predetermined clearance between the inner members. For fixing the suspension cross-member to vehicle body, a stud is inserted through the respective through holes and a nut is fitted onto a stud and screwed until the inner members abut each other.

15 Claims, 5 Drawing Sheets

SUSPENSION BUSHING, MOTOR VEHICLE AND A SUSPENSION CROSS-MEMBER FOR A MOTOR VEHICLE

BACKGROUND OF THE INVENTION

1. Field of the Invention

The present invention relates to a bushing, more particularly, to a bushing and a group of bushing for mounting a suspension cross-member on a vehicle, to a suspension cross-member fitted with such bushing, and to a vehicle on which such a suspension cross-member is mounted.

2. Description of the Related Art

Conventionally, bushing is used to mount a suspension cross-member to the bottom of a vehicle body. The structure of such bushing is disclosed in Japanese Patent Publication No. 2001-71944 for example, which comprises an outer member, an inner member which is inserted into the outer member and through which a stud on the body projects downwardly, and a elastic member disposed between the outer member and the inner member. In the structure, the bushing has an axial length sufficient for penetrating the cross-member and is press-fitted into respective mounting holes from one direction. To mount the cross-member to the body, the cross-member is fitted with the bushing, positioned in place with respect to the body so that the body studs are inserted into the inner member, and then secured to the body via nuts fitted onto the studs. The previous adjustment of a spring constant of the elastic member of the bushing achieves intended ride comfort and handling stability of the vehicle.

In a meantime, the application of a preload to the elastic member is well known for satisfying the needs of the ride comfort and the handling stability. For example, in the bushing structure constituted as described above, the elastic member has an extended axial length so as to protrude in the axial direction or in the vertical direction by a predetermined amount, and the nut is screwed until the elastic member is compressed between the body or the cross-member and the nut. Thus, after the cross-member is mounted on the body, the elastic member is provided with the predetermined amount of preload. In accordance with the structure as above, the elastic member is interposed between the body and the cross-member so as to be compressed in the vertical direction, so that the frequency dependence is reduced to improve the ride comfort, and the intended spring constant is produced in the elastic member. That is, the proper axial preload of the elastic member beneficially provides the vehicle with the increased ride comfort and handling stability at once.

The cross-member is supported on the body via a plurality of bushing, each of which is press-fitted into the cross-member and secured to the body. Accordingly, the variation in the amount of preload among the respective mounting portions or bushing may cause the degradation in the handling stability and ride comfort. To avoid the degradation, the accurate amount of preload should be applied to each bushing in the axial direction, thus measures are required for adjusting the screwing amount of each nut and for ensuring that the elastic member adequately deforms at the abutting portion on the body and the cross-member. Even with the measures described above, however, the variation in dimensional accuracy inevitably occurs in the cross-member or the bushing, which adversely affects the accuracy of the amount of the preload. Though the problem can be eliminated by precise management of the dimensional accuracy of parts, it causes the parts cost to rise and the production efficiency to decrease.

In addition, as disclosed in Japanese Patent Publication 2000-145854 for example, the bushing is typically fitted to bushing-attaching holes in suspension parts by press-fit operation. In the press-fit operation, a jig is used, which displaces the bushing in the fitting direction while abutting on the bushing. However, the jig may deform the bushing in the presence of friction between the bushing and the bushing-attaching hole, which also results in the variation in the amount of preload.

SUMMARY OF THE INVENTION

In view of the problem above, an object of the present invention is to achieve the excellent handling stability and ride comfort of the vehicle at once, by the provision of a bushing for mounting the cross-member to the bottom of the body which decreases the amount of the variation in preload for easily and reliably attaining the intended amount of preload with the reduced cost.

In accordance with the first aspect of the present invention, there is provided a bushing which is press-fitted into a top aperture and a bottom aperture of a bushing-attaching hole penetrating a suspension cross-member and fixed to a vehicular body by a stud and a nut for mounting the suspension cross-member to the bottom of the vehicular body. The bushing includes an outer member having an outer main body with a substantially cylindrical shape with an axial length shorter than one half of the axial length of the bushing-attaching hole of the suspension cross-member and an outer flange extending in the radially outward direction from an axial end of the outer main body, an inner member including an inner main body having a substantially cylindrical shape with an axial length longer than one half of the axial length of the bushing-attaching hole of the suspension cross-member and with an external diameter smaller than the internal diameter of the outer main body, an inner flange extending in the radially outward direction from an axial end of the inner main body with an external diameter larger than the internal diameter of the outer main body, and a through hole through which the stud can be inserted. The inner member is coaxially inserted into the outer member so that the inner flange and the outer flange are on the same side with respect to the axial direction and an elastic member is disposed between the inner member and the outer member and adhered to the inner main body, the inner flange, the outer main body, and the outer flange. When the bushing is press-fitted into the top aperture and the bottom aperture of the bushing-attaching hole until the outer flanges contact with the suspension cross-member before the bushing are fixed by the stud and the nut, the elastic members are substantially free from elastic deformation and provide a predetermined clearance between the other axial ends of the inner members. Moreover, when the bushing is fixed to the body by the stud and the nut, the elastic members are elastically deformed by tightening the nut fitted onto the stud so that the inner members are axially displaced with respect to the outer members to abut on each other.

Accordingly, for mounting the cross-member with a fastening mechanism, the bushing is press-fitted into the top aperture and the bottom aperture of the bushing-attaching hole, and the fastening mechanism is tightened until the ends of the inner members of the bushing abut on each other. Therefore, the operation as above easily provides an intended axial preload corresponding to the predetermined clearance in the bushing in a reliable manner with little or no variation in the amount of the preload among the bushing in respective bushing-attaching holes, after the cross-member is fixed to the body.

Preferably, the outer member further includes a jig-abutting portion provided in the outer flange, on which a jig can abut for press-fitting the bushing into a bushing-attaching hole in the suspension cross-member, and a reinforcing portion formed as a bending portion of the outer flange for preventing deformation of the outer member when the bushing is press-fitted with the jig.

Accordingly, in the press-fit operation, the reinforcing portion prevents deformation of the outer member due to the friction between the bushing and the bushing-attaching hole, which ensures the accurate amount of preload provided in the bushing.

Further it is preferred that the jig-abutting portion be a planar surface which continues to and is at substantially a right angle with the outer main body in a cross section including the central axis of the bushing.

Accordingly, in the press-fit operation, the jig can press the portion close to the outer main body of the outer flange, so that the deformation of the outer flange is avoided in combination with the effect of the reinforcing portion.

Still further it is preferable that the reinforcing portion include a slanted surface which is at an angle larger than the right angle with the outer main body, and the inner flange may include a tilt which faces the slanted surface substantially in parallel.

Accordingly, the elastic member is compressed by two surfaces facing in parallel with each other, so that the accuracy in preload provided in the bushing increases. Moreover, such an advantage is available by use of a part of the reinforcing portion.

In accordance with a second aspect of the present invention, there is provided a plurality of bushing.

In accordance with a third aspect of the present invention, there is provided a suspension cross-member fitted with bushing or a plurality of bushing.

In accordance with a forth aspect of the present invention, there is provided a vehicle on which a suspension cross-member is mounted.

These and other objects, features and advantages of the present invention will become more apparent upon reading of the following detailed description of preferred embodiments and accompanying drawings.

DETAILED DESCRIPTION OF THE INVENTION

A preferred embodiment of the present invention will now be described with reference to the drawings.

Figure 1:
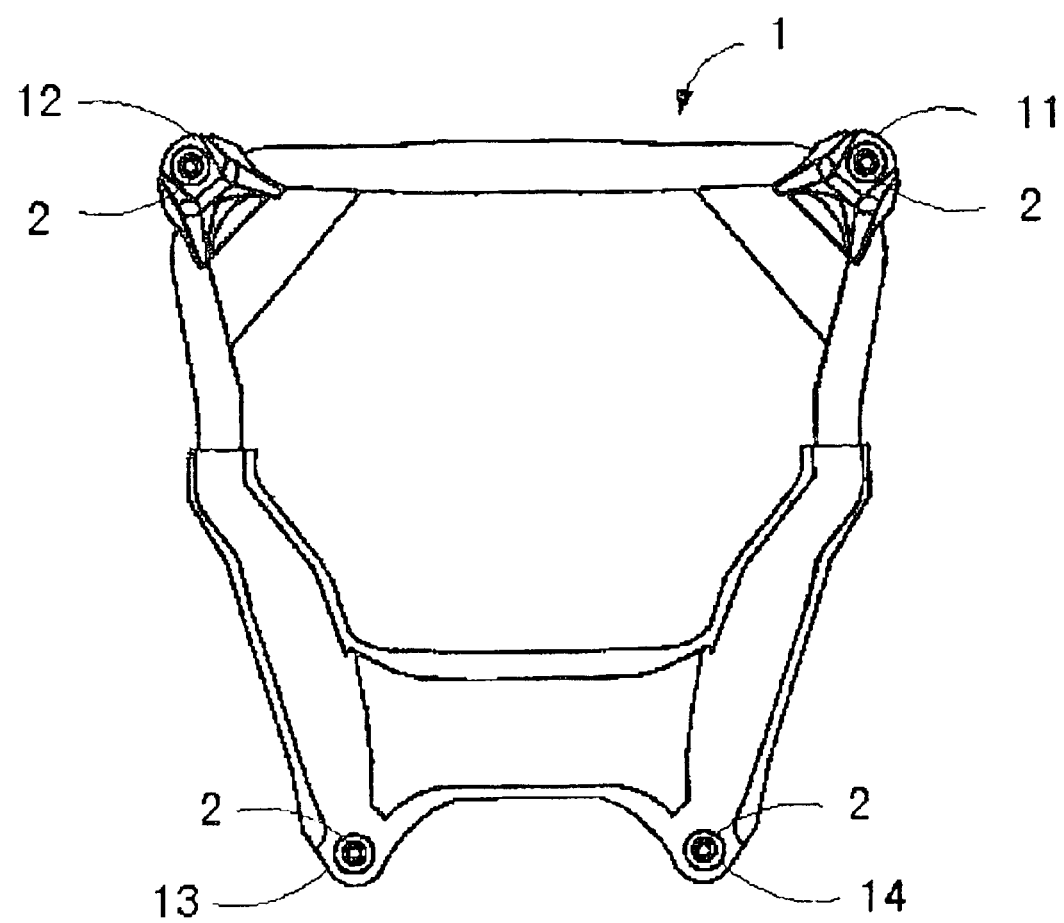
FIG. 1 is a top plan view of a front suspension cross-member mounted to a body via bushing in accordance with the present invention.

FIG. 1 is a top plan view of a front suspension cross-member (referred to as cross-member) 1 which is mounted to the body via three kinds of bushing 2a, 2b, and 2c (each of which is generally indicated as 2) in accordance with the present invention. As shown, the cross-member 1 is substantially rectangular in shape and includes flames with a closed cross-section. The cross-member 1 is formed with four bushing-attaching holes 11 to 14 into which bushing 2 are press-fitted. Though FIG. 1 shows bushing in the top surface of the cross-member, bushing are also press-fitted into the bottom surface of the cross-member. In the meantime, a vehicular body (not shown) is provided with four studs projecting therefrom, which are correspondingly arranged with respect to the location of the bushing 2. Thus, the cross-member 1, fitted with the bushing 2, is fixed to the body via the bushing by securing the bushing 2 onto the body with the studs and nuts.

The bushing 2 to be press-fitted into the bushing-attaching holes 11 to 14 are of split-type, and include a pair of halves split in the middle with respect to the axis before press-fitted. In other words, a pair of bushing 2 is each press-fitted into the top aperture and the bottom aperture of the respective bushing-attaching holes 11 to 14 of the cross-member 1.

The constitution of the bushing 2 will now be described with reference to FIGS. 2(a–c) to FIG. 4. As shown in FIGS. 2(a) to (c) illustrating plan views of the bushing 2, three kinds of bushing 2a to 2c are prepared which have through holes 224a, 224b, and 224c different from one another in shape, respectively. The difference will be described in detail below. As an example of the bushing 2, the constitution of the bushing 2a will now be described hereinbelow with reference to FIG. 2(a), because the constitution is common to the three except for the through holes 224a to 224c.

Figure 2:
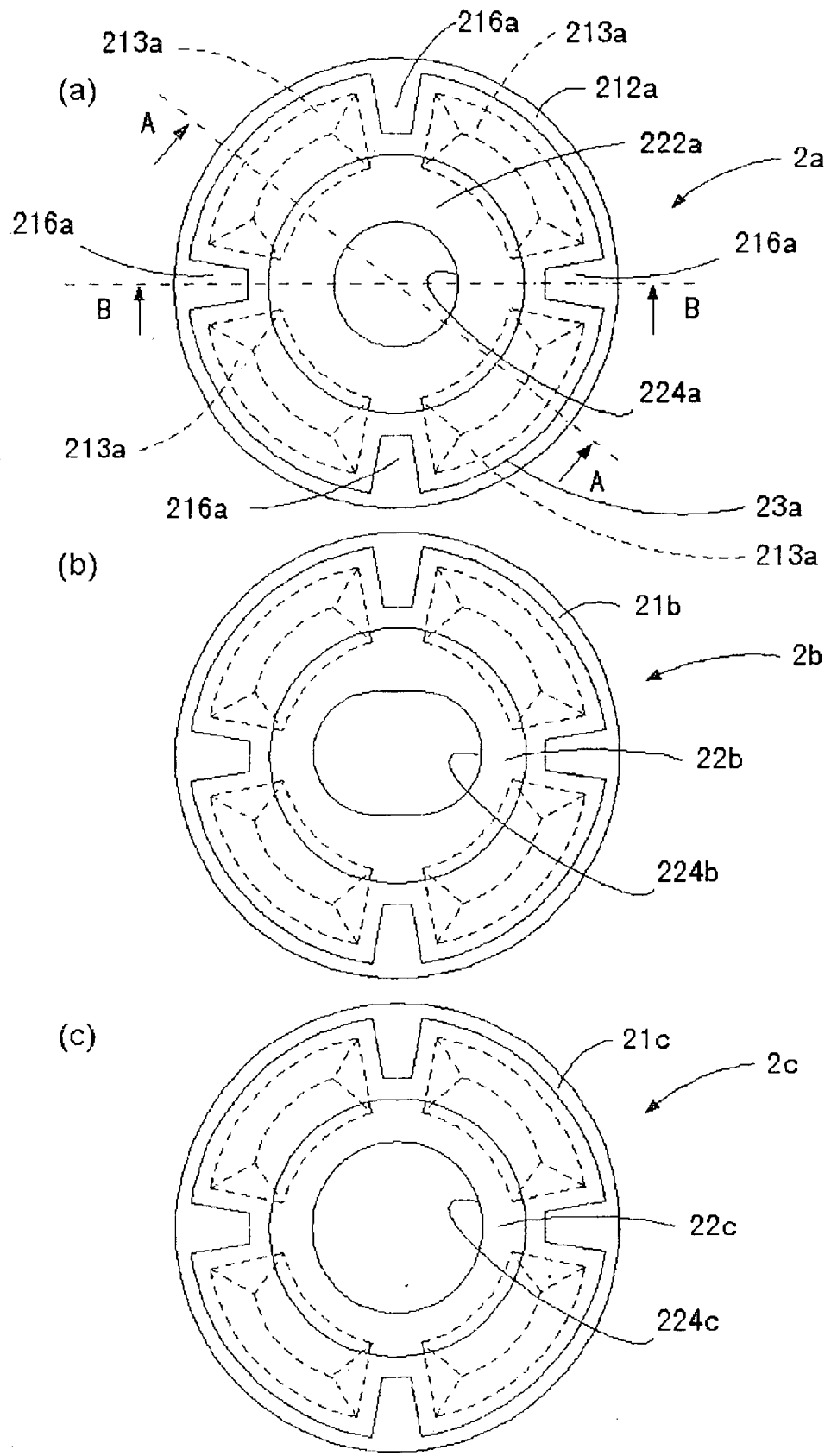
FIGS. 2(a–c) is a plan view of the bushing in accordance with the present invention.
Figure 3:
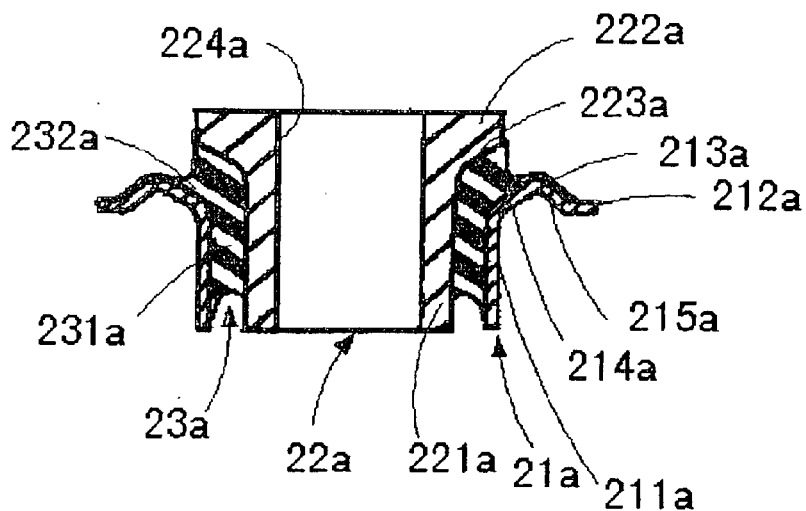
FIG. 3 is a cross-sectional view taken along A—A in FIGS. 2(a–c)
Figure 4:
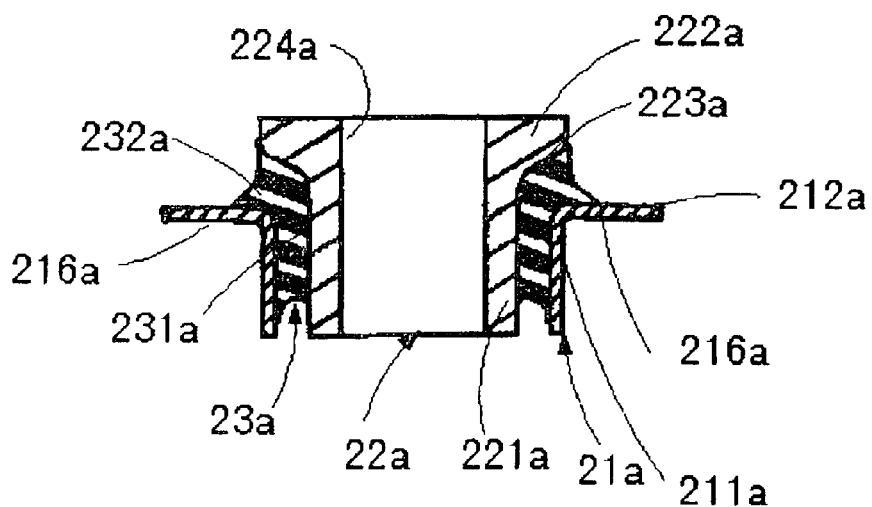
FIG. 4 is a cross-sectional view taken along B—B in FIGS. 2(a–c)

As shown in FIG. 3 illustrating a cross-sectional view taken along A—A in FIGS. 2(a–c), and in FIG. 4 illustrating a cross-sectional view taken along B—B in FIGS. 2(a–c), the bushing 2a includes a metallic outer member 21a, a metallic inner member 22a, and an elastic member 23a. The outer member 21a includes a cylindrical portion. The inner member 22a includes a cylindrical portion with an external diameter smaller than an internal diameter of the outer member 21a and with the through hole 224a through which the stud for mounting the cross-member is inserted. The elastic member is disposed between and adhered to both the outer member 21a and inner member 22a.

As shown in FIG. 3 and FIG. 4, the outer member 21a includes an outer main body 211a in a cylindrical shape with an internal diameter larger than the external diameter of the inner member 22a, and an outer flange 212a extending in the radially outward direction from an axial end of the main body 211a. The axial length of the outer member 21a is smaller than a half of the thickness of a portion where the bushing-attaching holes 11 to 14 for the bushing 2a are formed in the cross-member. The outer flange 212a is partially formed with reinforcing portions 213a along the circumferential direction of the flange. Particularly, as shown in FIGS. 2(a–c) in which the edge lines of the reinforcing portions 213a are indicated by broken lines, four reinforcing portions 213a are provided equally apart along the circumferential direction of the outer flange. Moreover, as shown in FIG. 3, the reinforcing portions 213a include an inner tilt 214a and outer tilt 215a which constitute bent portions of the flange, which protrudes away from the outer main body 211a. Further, as shown in FIG. 4, a flat surface between the four reinforcing portions 213a formed equally apart along the circumferential direction is approximately perpendicular to the outer main body 211a to provide a jig-abutting portion 216a.

As shown in FIG. 3 and FIG. 4, the inner member 22a includes a through bole 224a through which the stud for mounting the cross-member is inserted, an inner main body 221a in a cylindrical shape, and an inner flange 222a having an external diameter larger than the internal diameter of the outer main body 211a and extending in the radially outward direction from an axial end of the inner main body 221a. The inner member 22a is coaxially inserted into the outer member 21a so that the inner flange 222a and the outer flange 212a are coaxial, i.e., on the same side with respect to the axial direction. On a surface on the side of inner main body 221a of the inner flange 222a, a slanted surface 223a is provided along the circumferential direction, which continues to the inner main body 221a and is at the predetermined angle with the inner main body 221a. The slanted surface 223a is approximately parallel with the inner tilt 214a of the outer flange 212a. The axial length of the inner member 22a is longer than a half of the thickness of the portion where the bushing-attaching holes for this bushing in the cross-member.

Between the inner member 22a and the outer member 21a, the elastic member 23a, made from rubber, is disposed. As shown in FIG. 3 and FIG. 4, the elastic member includes an elastic main body 231a and an extending portion 232a which extends from an axial end of the elastic member. The elastic member 23a is adhered to the inner member 22a and the outer member 21a by bond applied over the contact surface thereof. The radially inner surface of the extending portion 232a contacts with the outer surface of the inner main body 221a and the slanted surface 223a, and the radially outer surface of the extending portion 232a contacts with the inner surface of the outer main body 211a and the reinforcing portion 213a of the outer flange 212a. Additionally, as shown in FIG. 2, the extending portion 232a is provided with covering portions which cover the reinforcing portion 213a. The covering portions of the elastic member 23a are adhered to the reinforcing portions 213a, which increases the peel resistance of the elastic member 23a from the outer member 21a. The jig-abutting portion 216a of the outer flange 212a, or the portions free of the reinforcing portion 213a in the outer flange 212a, are not covered with the elastic member.

This embodiment uses three kinds of bushing with the common structure as above and with the through holes of the inner member different in shape for mounting the cross-member 1 to the body. The shapes of through holes 224a, 224b, and 224c, and the assignment of the bushing 2a, 2b, and 2c to the cross-member 1 will now be described with reference to FIG. 1 and FIGS. 2(a–c).

As shown in FIG. 2(a), the through hole 224a is formed in the inner member 22a of the first bushing 2a. The cross-section of the through hole 224a is circular and substantially equal to the stud for mounting the cross member on the body in diameter. As shown in FIG. 2(b), the through hole 224b is formed in the inner member 22b of the second bushing 2b. The cross section of the through hole 224b is oblong, which is expanded in a direction perpendicular to the axial direction of the through hole from the through hole 224a of the first bushing 2a. As shown in FIG. 2(c), the through hole 224c is formed in the inner member 22c of the third bushing 2c. The cross-section of the through hole 224c is circular, which is expanded in all radial directions from the internal diameter of the 224a of the first bushing 2a. The outer member 21a, 21b, and 21c, and the elastic member 23a, 23b, and 23c are identical among the three bushing.

The three kinds of the bushing 2a, 2b, and 2c are assigned to the bushing-attaching holes 11 to 14 shown in FIG. 1 in the predetermined manner as follows:

1. In a reference bushing-attaching hole 11 which can be arbitrarily selected from the four holes, the first bushing 2a is press-fitted into one of the top aperture and the bottom aperture, and the third bushing 2c is press-fitted into the other.

2. In the bushing-attaching hole 12 which is laterally proximate to the reference attaching hole 11, the third bushing 2c is press-fitted into one of the top aperture and the bottom aperture, and the second bushing 2b is press-fitted into the other so that the expanded direction of the through holes of the bushing 2b is oriented towards the location of the first bushing 2a, or oriented in the vehicular lateral direction.

3. In the other bushing-attaching holes 13 and 14, the third bushing 2c is press-fitted into both the top apertures and the bottom apertures. That is, for mounting the cross-member, a group of eight bushing is used which includes one bushing 2a, one bushing 2b, and six bushing 2c.

With the assignment of the first bushing 2a, the second bushing 2b, and the third bushing 2c described as above, the cross-member 1 is positioned in the following manner. At the reference bushing-attaching hole 11, the first bushing 2a positions a point of the cross-member 1 in place. At the bushing-attaching 12 laterally proximate to the reference hole, the through hole 224b of the second bushing 2b allows the lateral misalignment between the body stud and the second bushing 2b because the expanded direction of the through hole 224b is oriented in the vehicular lateral direction, and positions the cross-member 1 in place in the vehicular longitudinal direction.

Thus, cross-member 1 is positioned in place with respect to the body. At the other bushing-attaching holes, the through holes of third bushing 2c allow both the lateral and longitudinal misalignments between the body stud and the third bushing 2c because the internal diameter of the third bushing 2c is expanded in all radial directions. Accordingly, the bushing press-fitted into the holes 11 to 14 of cross-member 1 are properly positioned with respect to the studs on the body frame, and the misalignments between the bushing and the studs are allowed at all the bushing-attaching holes.

As a result, the cross-member 1 is positioned in place with respect to the body and the interference of the studs with the bushing is avoided, so that the bushing are prevented from being horizontally biased after the cross-member is mounted to the body. In addition, only three kinds of bushing are required for positioning the cross-member in place.

Figure 5:
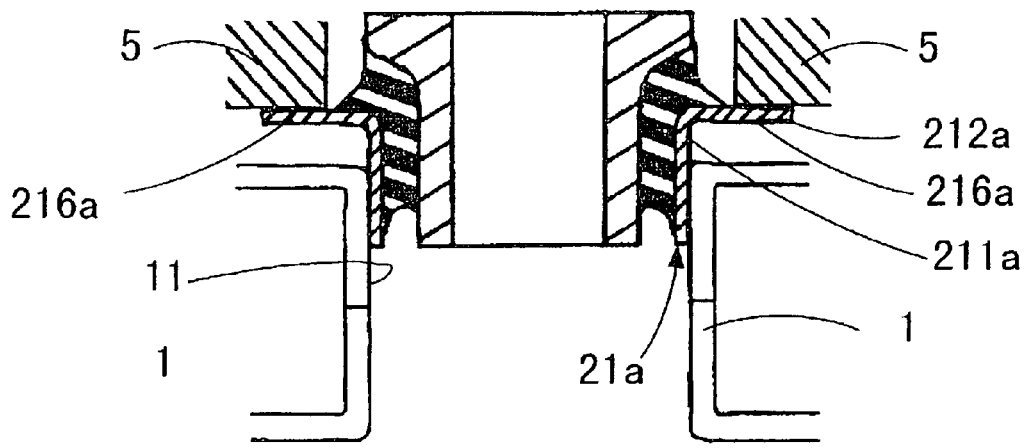
FIG. 5 is a cross-sectional view of bushing in press-fitting operation, corresponding to a cross-sectional view taken along B—B in FIGS. 2(a–c)
Figure 6:
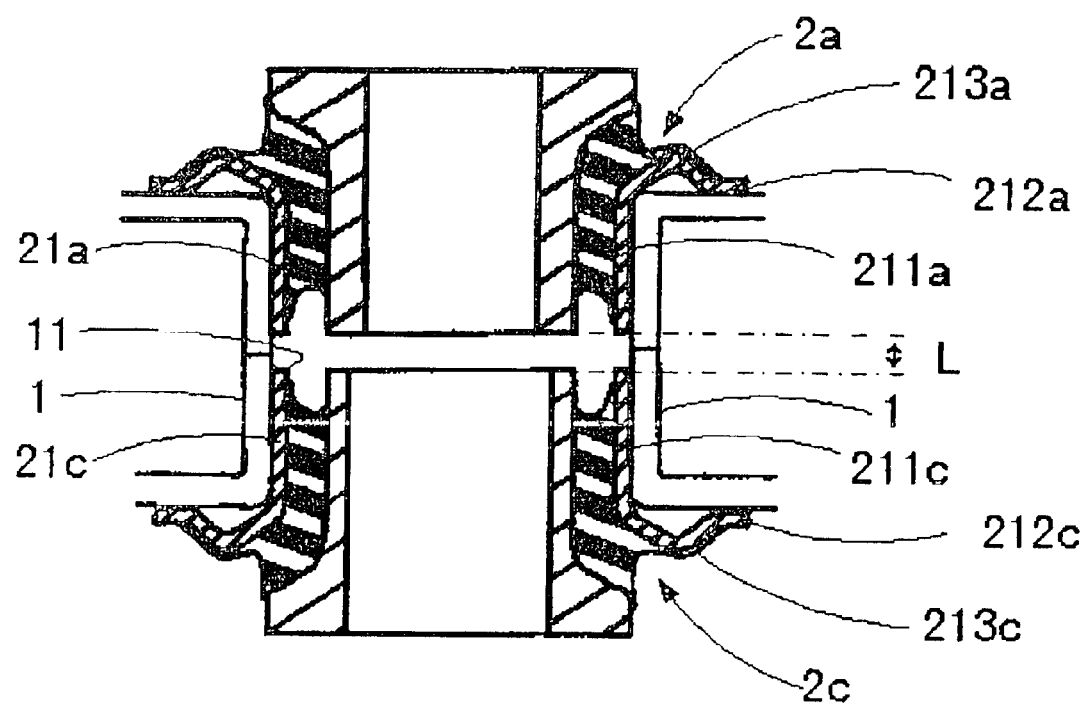
FIG. 6 is a cross-sectional view of press-fitted bushing, corresponding to a cross-sectional view taken along A—A in FIGS. 2(a–c)
Figure 7:
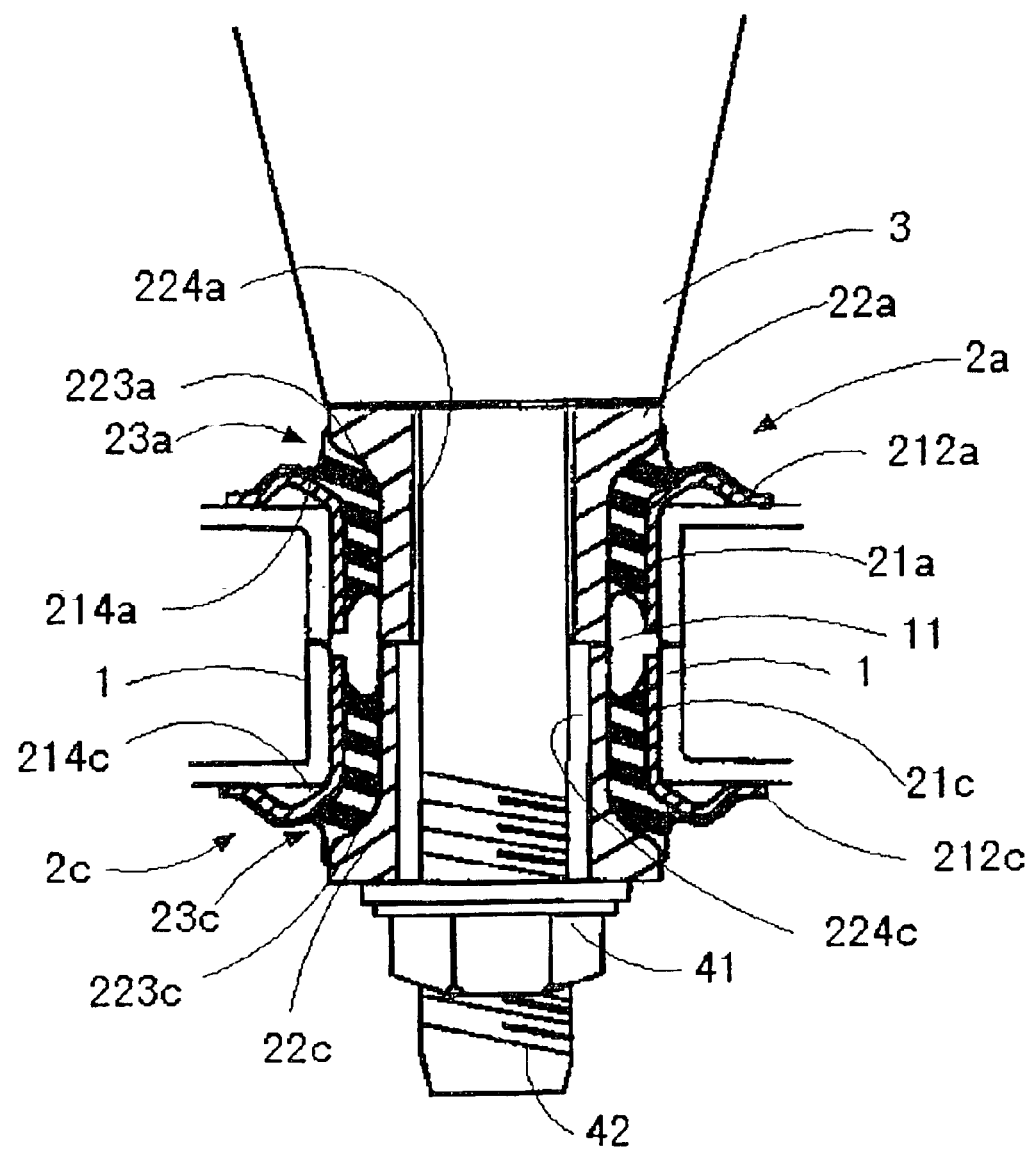
FIG. 7 is a cross-sectional view of a bushing secured to the body, corresponding to a cross-sectional view taken along A—A in FIGS. 2(a–c).

The press-fitting operation of the bushing 2 into the cross-member and the mounting operation of the cross-member 1 onto the body will now be described with reference to the FIG. 5 to FIG. 7 showing the bushing-attaching hole 11, by way of example.

The bushing 2a, 2b, and 2c are assigned in the manner as above and press-fitted into the bushing-attaching holes 11 to 14 of the cross-member 1, respectively. With regard to the bushing-attaching hole 11 for example, as shown in FIG. 6 showing a cross-sectional view taken along A—A in FIGS. 2(a–c), the bushing 2a is press-fitted into the top aperture and the bushing 2c is press-fitted into the bottom aperture. Then, the cross-member 1 fitted with the bushing 2a to 2c is positioned so that the studs 42 on the body 3 are inserted into the through holes 224a to 224c of the bushing 2a to 2c. Thereafter, the nuts 41 are fitted onto the studs 42 for fixing the bushing, as a result, the cross-member 1 is fixed to the body 3 via the bushing. With regard to the bushing-attaching hole 11 for example, the condition after the cross-member 1 is fixed to the body is illustrated in FIG. 7 showing a cross-sectional view taken along A—A in FIGS. 2(a–c). Before fixed to the body 3, the cross-member is previously fitted with suspension arms supporting wheel hubs, coil dampers, stabilizers, or other parts (not shown).

As shown in FIG. 5, in the press-fitting operation of the bushing 2a into the bushing-attaching hole 11, the jig 5 abuts onto the jig-abutting portion 216a in the outer flange 212a, and displaces the bushing 2a until the outer flange 212a comes into contact with the top surface of the cross-member 1. Likewise, as for the bushing 2c, the jig 5 abuts onto the jig-abutting portion 216c in the outer flange 212c, and displaces the bushing 2c until the outer flange 212a comes into contact with the bottom surface of the cross-member 1.

Accordingly, with regard to the bushing 2a in the top aperture for example, the jig 5 presses the portion close to the central axis of the bushing 2 between the reinforcing portions 213a of the outer flange. Thus, the deformation of the outer member 21a, particularly, the deformation at the connecting portion of the outer main body 211a and the outer flange 212a due to the friction during the press-fitting operation is prevented in conjunction with the effect of the reinforcing portion 213a. Likewise, with regard to the bushing 2c in the bottom aperture, the deformation at the connecting portion of the outer main body 211c and the outer flange 212c is prevented. Then, after the cross-member 1 is fitted with the bushing 2a and 2c before mounted to the body, there exists a clearance L between both the inner members, as shown in FIG. 6.

With regard to the other bushing-attaching holes 12 to 14, as with the bushing-attaching hole 11, the bushing 2b and 2c are assigned as above and press-fitted, then there exist the predetermined clearances between the inner members after the bushing are press-fitted.

The cross-member 1 fitted with the bushing 2a to 2c and the parts as above are fixed to the body via the bushing 2a to 2c. In the bushing-attaching hole 11 for example, as shown in FIG. 7, the stud 42 is inserted through the respective through holes 224a and 224c of the press-fitted bushing 2a and 2c, and then the nuts 41 is fitted onto the stud 42 for fixing the bushing 2 so that the cross-member 1 is fixed to the body 3 via the bushing 2a and 2c. The nut 41 is screwed so as to cause the inner member 22a of the upper bushing 2a and the inner member 22c of the lower bushing 2c to be displaced with respect to the outer member 21a and 21c, until the inner members abut on each other. After the nut is screwed as above, the elastic member 23a of the upper bushing and the elastic member 23c and the lower bushing are compressed vertically between the inner member 22a and the outer member 21a, and between the inner member 22c and the outer member 21c by the predetermined amount corresponding to the clearance L, respectively. Thus, there is provided axial or vertical preload corresponding to the compression in the bushing.

Accordingly, whenever the distance between the top surface and the bottom surface of the portion of the cross-member 1 with which the outer flange 212a and 212c contact is accurate, the predetermined vertical preload corresponding to the compression by the clearance L is easily and reliably applied to the bushing 2a and 2c, by screwing the nut 41 until the inner member 22a of the bushing 2a and the inner member 22c of the bushing 2c abut on each other.

With regard to the other bushing-attaching holes 12 to 14, as with the bushing-attaching hole 11, the studs are inserted through the through hole 224b of the bushing 2b and the through hole 224c of and the bushing 2c, and the nut is screwed until the inner members abut on each other.

Accordingly, the setting the clearance L to the amount for the proper preload enables the bushing press-fitted into the respective bushing-attaching holes to be provided with the proper amount of preload with little or no variation among the bushing. Additionally, the slanted surface of the inner flange and the inner tilt of the reinforcing portion are substantially parallel with each other, so that the preload is more evenly applied to the elastic member between the slanted surface and the inner tilt. Moreover, the two surfaces are faced with each other, which causes little variation in deformation or little variation in the amount of preload among the elastic members in respective bushing-attaching holes, thereby contributing to the accuracy.

Although the present invention has been described in relation to particular embodiments thereof, many other variations and modifications and other uses will become apparent to those skilled in the art. It is preferred therefore, that the present invention be limited not by the specific disclosure herein, but only by the appended claims. For example, though the bushing according to the preferred embodiment of the present invention is used for the front cross-member, it would be obvious to those skilled in the art that the bushing may be used for a rear cross-member and the identical advantage is available then.

What is claimed is:

1. A bushing adapted to be press-fit into a top aperture and a bottom aperture of a bushing-attaching hole to mount a suspension cross-member to a vehicular body via a stud and nut arrangement, said bushing comprising:
   an outer member including an outer main body having a substantially cylindrical shape with an axial length shorter than one half the axial length of the bushing-attaching hole, and an outer flange extending in a radially outward direction from an axial end of said outer main body;
   an inner member including an inner main body having a substantially cylindrical shape with an axial length longer than one half the axial length of the bushing-attaching hole with an external diameter smaller than the internal diameter of said outer main body, an inner flange extending in a radially outward direction from an axial end of said inner main body with an external diameter larger than the internal diameter of said outer main body, and a through hole through which the stud is inserted, said inner member being inserted into said outer member so that said inner flange and said outer flange lie coaxially relative to each other;
   an elastic member disposed between said inner member and said outer member and adhered to each one of said inner main body, said inner flange, said outer main body, and said outer flange,
   wherein said elastic members is substantially free from elastic deformation to provide a predetermined clearance between the axial end of said inner member when said bushing is press-fit into the bushings-attaching hole until the outer flanges contact the suspension cross-member before said bushing is fixed by the stud and nut arrangement, and
   wherein said elastic member is elastically deformed by tightening the stud and nut arrangement so that said inner member is axially displaced with respect to said outer member so that they abut each other when the suspension cross-member is mounted to the vehicle body.

2. The bushing as defined in claim 1, wherein said outer member further includes a jig-abutting portion provided on said outer flange so that a jig can abut to permit the press-fitting of said bushing into the bush-attaching hole, and a reinforcing portion formed as a bending portion on said outer flange for preventing deformation of said outer member when said bushing is press-fit with the jig.

3. The bushing as defined in claim 2, wherein said jig-abutting portion has a planar surface which lies at a substantially right angle relative to said outer main body in an area including the central axis of said bushing.

4. The bushing defined in claim 3, wherein said reinforcing portion includes a slanted surface which lies at an angle larger than that of said planar surface with respect to said outer main body, and said inner flange includes a tilt which faces said slanted surface substantially in parallel.

5. The bushing as defined in of claim 1, wherein said bushing comprises at least three bushing adapted to be press-fit into top apertures and bottom apertures of a respective bushing-attaching hole, said at least three bushing including a first bushing, a second bushing and a third bushing, wherein said first bushing has a through hole with an internal diameter approximately equal to an external diameter of a respective stud, said second bushing has an oblong-shaped through hole in cross-section which expands in a radial direction and an internal diameter approximately equal to an external diameter of a respective stud, and said third bushing has a circular-shaped through hole in cross-section that expands in all radial directions and an internal diameter approximately equal to an external diameter of a respective stud.

6. A suspension cross-member adapted to be mounted to a vehicle body via a stud and nut arrangement, said suspension cross-member comprising:

a bushing-attaching hole forming a top aperture and a bottom aperture on the top surface and the bottom surface of the suspension cross-member; and a pair of bushings which are press-fit into said top aperture and said bottom aperture, respectively, said pair of bushings including:

an outer member having an outer main body with a substantially cylindrical shape with an axial length shorter than one half the axial length of said bushing-attaching hole, and an outer flange extending in a radially outward direction from an axial end of said outer main body;

an inner member having an inner main body with a substantially cylindrical shape and an axial length longer than one half the axial length of the bushing-attaching hole with an external diameter smaller than the internal diameter of said outer main body, an inner flange extending in a radially outward direction from an axial end of said inner main body, said inner flange having an external diameter larger than the internal diameter of said outer main body, and a through hole through which the stud is inserted, said inner member being inserted into said outer member so that said inner flange and said outer flange lie coaxially with respect to each other; and an elastic member disposed between said inner member and said outer member, said elastic member being adhered to each one of said inner main body, said inner flange, said outer main body, and said outer flange, wherein said elastic member is substantially free from elastic deformation and provides a predetermined clearance between the axial end of said inner member when said pair of bushing is press-fit into said bushing-attaching hole until said outer flange contacts said suspension cross-member before said pair of bushing are fixed by the stud and nut arrangement, and wherein said elastic member is elastically deformed by tightening the stud and nut arrangement so that said inner member is axially displaced with respect to said outer member so that they abut each other when said suspension cross-member is mounted to the vehicle body.

7. A suspension cross-member adapted to be mounted to a vehicle body via a stud and nut arrangement, said suspension cross-member comprising:

at least three bushing-attaching holes which form top apertures and bottom apertures on the top surface and the bottom surface of said suspension cross-member; and at least six bushings which are press-fit into said top apertures and said bottom apertures, respectively, said six bushing including:

an outer member having an outer main body with a substantially cylindrical shape and an axial length shorter than one half of the axial length of a respective bushing-attaching hole and an outer flange extending in a radially outward direction from an axial end of said outer main body;

an inner member having an inner main body with a substantially cylindrical shape and an axial length longer than one half of the axial length of a respective bushing-attaching hole and with an external diameter smaller than the internal diameter of said outer main body, an inner flange extending in a radially outward direction from an axial end of said inner main body with an external diameter larger than the internal diameter of said outer main body, and a through hole through which the stud is inserted, said inner member being inserted into said outer member so that said inner flange and said outer flange lie coaxially; and an elastic member disposed between said inner member and said outer member and adhered to each one of said inner main body, said inner flange, said outer main body, and said outer flange, wherein said elastic member is substantially free from elastic deformation and provides a predetermined clearance between the axial end of said inner member when said bushing is press-fit into a respective bushing-attaching hole until said outer flange contacts the suspension cross-member before said at least six bushing are fixed by the stud and nut arrangement, and wherein said elastic member is elastically deformed by tightening the stud and nut arrangement so that said inner member is axially displaced with respect to said outer member so that they abut each other when the suspension cross-member is mounted to the vehicle body, wherein said first bushing has a through hole with an internal diameter approximately equal to an external diameter of a respective stud, said second bushing has an oblong-shaped through hole in cross-section which expands in a radial direction and an internal diameter approximately equal to an external diameter of a respective stud, and said third bushing has a circular-shaped through hole in cross-section that expands in all radial directions and an internal diameter approximately equal to an external diameter of a respective stud, and wherein each one of said at least six bushings is press-fit in such a manner that the first bushing is press-fit into one of said top aperture and said bottom aperture of the first bushing-attaching hole of said at least three bushing-attaching holes, the second bushing is press-fit into one of said top aperture and said bottom aperture of the second bushing-attaching hole of said at least three bushing-attaching holes so that an expanded direction of said through hole of said second bushing is oriented substantially towards said first bushing-attaching hole, and the third bushing is press-fit into the other aperture of said first bushing-attaching hole, the other aperture of said second bushing-attaching hole, and both said top aperture and said bottom aperture of the third bushing-attaching hole of said at least three bushing-attaching holes.

8. A vehicle comprising:

a vehicle body;

a suspension cross-member mounted to said vehicle body via a stud and nut arrangement, said suspension cross-member including a bushing-attaching hole which penetrates said suspension cross-member to form a top aperture and a bottom aperture on the top surface and the bottom surface of said suspension cross-member, respectively; and a pair of bushings which are press-fit into said top aperture and said bottom aperture, respectively, said bushings including:

an outer member having an outer main body with a substantially cylindrical shape and an axial length shorter than one half of the axial length of said bush-attaching hole of said suspension cross-member and an outer flange extending in a radially outward direction from an axial end of said outer main body;

an inner member having an inner main body with a substantially cylindrical shape and an axial length longer than one half of the axial length of said bush-attaching hole of said suspension cross-member and with an external diameter smaller than the internal diameter of said outer main body, an inner flange extending in a radially outward direction from an axial end of said inner main body with an external diameter larger than the internal diameter of said outer main body, and a through hole through which the stud can be inserted, said inner member being coaxially inserted into said outer member so that said inner flange and said outer flange are coaxial; and an elastic member disposed between said inner member and said outer member and adhered to said inner main body, said inner flange, said outer main body, and said outer flange, wherein said elastic member is substantially free from elastic deformation and provides a predetermined clearance between the opposite axial ends of said inner members when each one of said pair of bushings is press-fit into said top aperture and said bottom aperture of said bush-attaching hole until said outer flange contacts said suspension cross-member before said pair of bushing are fixed by the stud and nut arrangement, and said elastic member is elastically deformed by tightening the nut onto the stud so that said inner member is axially displaced with respect to said outer member so as to abut each other when each one of said pair of bushings is fixed to the body by the stud and nut arrangement.

9. A vehicle comprising:

a vehicle body;

a suspension cross-member mounted to said vehicle body via a stud and nut arrangement, said suspension cross-member comprising:

at least three bushing-attaching holes which form top apertures and bottom apertures on the top surface and the bottom surface of said suspension cross-member; and at least six bushings which are press-fit into said top apertures and said bottom apertures, respectively, said at least six bushings including:

an outer member having an outer main body with a substantially cylindrical shape and an axial length shorter than one half of the axial length of a respective bushing-attaching hole and an outer flange extending in a radially outward direction from an axial end of said outer main body;

an inner member having an inner main body with a substantially cylindrical shape and an axial length longer than one half of the axial length of a respective bushing-attaching hole and with an external diameter smaller than the internal diameter of said outer main body, an inner flange extending in a radially outward direction from an axial end of said inner main body with an external diameter larger than the internal diameter of said outer main body, and a through hole through which the stud is inserted, said inner member being inserted into said outer member so that said inner flange and said outer flange lie coaxially; and an elastic member disposed between said inner member and said outer member and adhered to each one of said inner main body, said inner flange, said outer main body, and said outer flange, wherein said elastic member is substantially free from elastic deformation and provides a predetermined clearance between the axial end of said inner member when said bushing is press-fit into a respective bushing-attaching hole until said outer flange contacts said suspension cross-member before said at least three pair of bushings are fixed by said stud and nut arrangement, wherein said elastic member is elastically deformed by tightening said stud and nut arrangement so that said inner member is axially displaced with respect to said outer member so that they abut each other when said suspension cross-member is mounted to said vehicle body, wherein said first bushing has a through hole with an internal diameter approximately equal to an external diameter of a respective stud, said second bushing has an oblong-shaped through hole in cross-section which expands in a radial direction and an internal diameter approximately equal to an external diameter of a respective stud, and said third bushing has a circular-shaped through hole in cross-section that expands in all radial directions and an internal diameter approximately equal to an external diameter of a respective stud, and wherein each one of said at least six bushings is press-fit in such a manner that the first pair of bushings is press-fit into one of said top apertures and said bottom apertures of the first bushing-attaching hole of said at least three bush-attaching holes, the second bushing is press-fit into one of said top apertures and said bottom apertures of the second bushing-attaching hole of said at least three bushing-attaching holes so that an expanded direction of said through hole of said second bushing is oriented substantially towards said first bushing-attaching hole, and the third bushing is press-fit into the other aperture of said first bushing-attaching hole, the other aperture of the second bushing-attaching hole, and both said top apertures and said bottom apertures of the third bushing-attaching hole of said at least three bushing-attaching holes.

10. A bushing adapted to be press-fit into a top aperture and a bottom aperture of a bushing-attaching hole of a suspension cross-member with a jig and fixed to a vehicle body by a stud and nut arrangement for mounting the suspension cross-member to the vehicle body, said bushing comprising:

an outer member including an outer main body with a substantially cylindrical shape and an axial length shorter than one half of the axial length of the bushing-attaching hole and an outer flange extending in a radially outward direction from an axial end of said outer main body, said outer flange being provided with a jig-abutting portion having a planar surface lying at a substantially right angle relative to said outer main body in an area including the central axis of said bushing and on which the jig can abut for press-fitting said bushing into the bushing-attaching hole, and a reinforcing portion formed as a bending portion including a slanted surface which lies at an angle larger than said planar surface relative to said outer main body of said outer flange;

an inner member including an inner main body with a substantially cylindrical shape, an axial length longer than one half of the axial length of the bushing-attaching hole, and an external diameter smaller than the internal diameter of said outer main body, an inner flange extending in a radially outward direction from an axial end of said inner main body with an external diameter larger than the internal diameter of said outer main body and having a tilt provided on the side of the opposite axial end of said inner flange, and a through hole through which the stud is inserted, said inner member being coaxially inserted into said outer member so that said inner flange and said outer flange are coaxial and said tilt faces said slanted surface of said outer flange substantially in parallel;

an elastic member disposed between said inner member and said outer member and adhered to said inner main body, said inner flange, said outer main body, and said outer flange, wherein said elastic member is substantially free from elastic deformation and provide a predetermined clearance between the opposite axial ends of said inner member when said bushing is press-fit into the top aperture and the bottom aperture of the bushing-attaching hole until said outer flange contacts the suspension cross-member before said bushing is fixed by the stud and nut arrangement, and said elastic member is elastically deformed by tightening the nut fitted onto the stud so that said inner member is axially displaced with respect to said outer member so as to abut each other when said bushing is fixed to the body by the stud and the nut.

11. The bushing as defined in claim 10, wherein said bushing comprises at least three bushings adapted to be press-fit into top apertures and bottom apertures of a respective bushing-attaching hole, said at least three bushings including a first bushing, a second bushing and a third bushing, wherein said first bushing has a through hole with an internal diameter approximately equal to an external diameter of a respective stud, said second bushing has an oblong-shaped through hole in cross-section which expands in a radial direction and an internal diameter approximately equal to an external diameter of a respective stud, and said third bushing has a circular-shaped through hole in cross-section that expands in all radial directions and an internal diameter approximately equal to an external diameter of a respective stud.

12. A suspension cross-member adapted to be mounted to a vehicle body via a stud and nut arrangement, said suspension cross-member comprising:

a bushing-attaching hole which penetrates said suspension cross-member to form a top aperture and a bottom aperture on the top surface and the bottom surface of said suspension cross-member, respectively; and a pair of bushings which are press-fit into said top aperture and said bottom aperture, respectively, said pair of bushings including:

an outer member having an outer main body with a substantially cylindrical shape and an axial length shorter than one half of the axial length of said bushing-attaching hole and an outer flange extending in a radially outward direction from an axial end of said outer main body, said outer flange being provided with a jig-abutting portion having a planar surface lying at a substantially right angle relative to said outer main body in an area including the central axis of said bushing and on which a jig abuts for press-fitting said bushing into a bushing-attaching hole, and a reinforcing portion formed as a bending portion including a slanted surface which lies at an angle larger than said planar surface relative to said outer main body of said outer flange;

an inner member having an inner main body with a substantially cylindrical shape, an axial length longer than one half of the axial length of said bushing-attaching hole, and an external diameter smaller than the internal diameter of said outer main body, an inner flange extending in a radially outward direction from an axial end of said inner main body with an external diameter larger than the internal diameter of said outer main body and having a tilt provided on the side of the opposite axial end of said inner flange, and a through hole through which the stud is inserted, said inner member being coaxially inserted into said outer member so that said inner flange and said outer flange are coaxial and said tilt faces said slanted surface of said outer flange substantially in parallel;

an elastic member disposed between said inner member and said outer member and adhered to said inner main body, said inner flange, said outer main body, and said outer flange, wherein said elastic member is substantially free from elastic deformation and provides a predetermined clearance between the opposite axial ends of said inner members when said bushing is press-fit into said top aperture and said bottom aperture of said bushing-attaching hole until said outer flange contacts said suspension cross-member before said bushing are fixed by the stud and nut arrangement, and said elastic member is elastically deformed by tightening the nut on the stud so that said inner member is axially displaced with respect to said outer member so as to abut each other when said bushing is fixed to the body by the stud and nut arrangement.

13. A suspension cross-member adapted to be mounted to a vehicle body via a stud and nut arrangement, said suspension cross-member comprising:

at least three bushing-attaching holes which penetrate said suspension cross-member to form top apertures and bottom apertures on the top surface and the bottom surface of said suspension cross-member, respectively; and at least six bushings which are press-fit into said top apertures and said bottom apertures, respectively, said at least six bushing includings:

an outer member including an outer main body with a substantially cylindrical shape and an axial length shorter than one half of the axial length of said bushing-attaching hole and an outer flange extending in a radially outward direction from an axial end of said outer main body, said outer flange being provided with a jig-abutting portion having a planar surface lying at a substantially right angle relative to said outer main body in an area including the central axis of said bushing and on which a jig can abut for press-fitting said bushing into a respective bushing-attaching hole, and a reinforcing portion formed as a bending portion including a slanted surface which lies at an angle larger than said planar surface relative to said outer main body of said outer flange;

an inner member including an inner main body with a substantially cylindrical shape, an axial length longer than one half of the axial length of said bushing-attaching hole, and an external diameter smaller than the internal diameter of said outer main body, an inner flange extending in a radially outward direction from an axial end of said inner main body with an external diameter larger than the internal diameter of said outer main body and having a tilt provided on the side of the opposite axial end of said inner flange, and a through hole through which the stud is inserted, said inner member being coaxially inserted into said outer member so that said inner flange and said outer flange are coaxial and said tilt faces said slanted surface of said outer flange substantially in parallel; and an elastic member disposed between said inner member and said outer member and adhered to said inner main body, said inner flange, said outer main body, and said outer flange, wherein said elastic member is substantially free from elastic deformation and provides a predetermined clearance between the opposite axial ends of said inner member when said bushing is press-fit into a respective top aperture and bottom aperture of said bushing-attaching hole until said outer flange contacts said suspension cross-member before said bushing are fixed by the stud and nut arrangement, and said elastic member is elastically deformed by tightening the nut on the stud so that said inner member is axially displaced with respect to said outer member so as to abut each other when said bushing is fixed to the body by the stud and nut arrangement, wherein said at least six bushings includes a first bushing having a through hole with an internal diameter approximately equal to an external diameter of a respective stud, a second bushing having an oblong-shaped through hole in cross-section which expands in a radial direction and an internal diameter approximately equal to an external diameter of a respective stud, and a third bushing having a circular-shaped through hole in cross-section that expands in all radial directions and an internal diameter approximately equal to an external diameter of a respective stud, wherein each one of said at least six bushings is press-fit in such a manner that the first bushing is press-fit into one of said top aperture and said bottom aperture of the first bushing-attaching hole of said at least three bushing-attaching holes, the second bushing is press-fit into one of said top aperture and said bottom aperture of the second bushing-attaching hole of said at least three bushing-attaching holes so that an expanded direction of said through hole of said second bushing is oriented substantially towards said first bushing-attaching hole, and the third bushing is press-fit into the other aperture of said first bushing-attaching hole, the other aperture of said second bushing-attaching hole, and both said top aperture and said bottom aperture of the third bushing-attaching hole of said at least three bushing-attaching holes.

14. A vehicle comprising:

a vehicle body; and a suspension cross-member mounted to said vehicle body via a stud and nut arrangement, said suspension cross-member including a bushing-attaching hole which penetrates said suspension cross-member to form a top aperture and a bottom aperture on the top surface and the bottom surface of said suspension cross-member, respectively, and a pair of bushings which are press-fit into said top aperture and said bottom aperture, respectively, said pair of bushings including:

an outer member having an outer main body with a substantially cylindrical shape and an axial length shorter than one half of the axial length of said bushing-attaching hole and an outer flange extending in a radially outward direction from an axial end of said outer main body, said outer flange being provided with a jig-abutting portion having a planar surface lying at a substantially right angle relative to said outer main body in an area including the central axis of said pair of bushing and on which a jig can abut for press-fitting said pair of bushing into a respective bushing-attaching hole, and a reinforcing portion formed as a bending portion including a slanted surface which lies at an angle larger than said planar surface relative to said outer main body of said outer flange;

an inner member including an inner main body with a substantially cylindrical shape, an axial length longer than one half of the axial length of the respective bushing-attaching hole, and an external diameter smaller than the internal diameter of said outer main body, said inner member further including an inner flange extending in a radially outward direction from an axial end of said inner main body with an external diameter larger than the internal diameter of said outer main body and having a tilt provided on the side of the opposite axial end of said inner flange, and a through hole through which the stud is inserted, said inner member being coaxially inserted into said outer member so that said inner flange and said outer flange are coaxial and said tilt faces said slanted surface of said outer flange substantially in parallel;

an elastic member disposed between said inner member and said outer member and adhered to said inner main body, said inner flange, said outer main body, and said outer flange, wherein said elastic member is substantially free from elastic deformation and provides a predetermined clearance between the opposite axial ends of said inner member when said pair of bushings is press-fit into said top aperture and said bottom aperture of their respective bushing-attaching hole until said outer flanges contact said suspension cross-member before said pair of bushing are fixed by the stud and the nut, and said elastic member is elastically deformed by tightening the nut on the stud so that said inner member is axially displaced with respect to said outer member so as to abut each other when said bushing is fixed to said vehicle body by the stud and nut arrangement.

15. A vehicle comprising:

a vehicle body; and a suspension cross-member mounted to said vehicle body via a stud and nut arrangement, said suspension cross-member comprising:

at least three bushing-attaching holes which penetrate said suspension cross-member to form top apertures and bottom apertures on the top surface and the bottom surface of said suspension cross-member, respectively, at least six bushings which are press-fit into said top apertures and said bottom apertures of said at least three bushing-attaching holes, said at least six bushings including:

an outer member including an outer main body with a substantially cylindrical shape and an axial length shorter than one half of the axial length of said bushing-attaching hole and an outer flange extending in a radially outward direction from an axial end of said outer main body, said outer flange being provided with a jig-abutting portion having a planar surface lying at a substantially right angle relative to said outer main body in an area including the central axis of said bushing and on which a jig can abut for press-fitting said bushing into a respective bushing-attaching hole, and a reinforcing portion formed as a bending portion including a slanted surface which lies at an angle larger than said planar surface relative to said outer main body of said outer flange;

an inner member including an inner main body with a substantially cylindrical shape, an axial length longer than one half of the axial length of said bushing-attaching hole, and an external diameter smaller than the internal diameter of said outer main body, an inner flange extending in a radially outward direction from an axial end of said inner main body with an external diameter larger than the internal diameter of said outer main body and having a tilt provided on the side of the opposite axial end of said inner flange, and a through hole through which the stud is inserted, said inner member being coaxially inserted into said outer member so that said inner flange and said outer flange are coaxial and said tilt faces said slanted surface of said outer flange substantially in parallel; and an elastic member disposed between said inner member and said outer member and adhered to said inner main body, said inner flange, said outer main body, and said outer flange, wherein said elastic member is substantially free from elastic deformation and provides a predetermined clearance between the opposite axial ends of said inner member when said bushing is press-fit into a respective top aperture and bottom aperture of said bushing-attaching hole until said outer flange contacts said suspension cross-member before said bushing are fixed by the stud and nut arrangement, and said elastic member is elastically deformed by tightening the nut on the stud so that said inner member is axially displaced with respect to said outer member so as to abut each other when said bushing is fixed to the body by the stud and nut arrangement, wherein said at least six bushing includes a first bushings having a through hole with an internal diameter approximately equal to an external diameter of a respective stud, a second bushing having an oblong-shaped through hole in cross-section which expands in a radial direction and an internal diameter approximately equal to an external diameter of a respective stud, and a third bushing having a circular-shaped through hole in cross-section that expands in all radial directions and an internal diameter approximately equal to an external diameter of a respective stud, wherein each one of said at least six bushings is press-fit in such a manner that the first bushing is press-fit into one of said top aperture and said bottom aperture of the first bushing-attaching hole of said at least three bushing-attaching holes, the second bushing is press-fit into one of said top aperture and said bottom aperture of the second bushing-attaching hole of said at least three bushing-attaching holes so that an expanded direction of said through hole of said second bushing is oriented substantially towards said first bushing-attaching hole, and the third bushing is press-fit into the other aperture of said first bushing-attaching hole, the other aperture of said second bushing-attaching hole, and both said top aperture and said bottom aperture of the third bushing-attaching hole of said at least three bushing-attaching holes.

\* \* \* \* \*